United States Patent [19]
Olsson et al.

[11] Patent Number: 5,720,277
[45] Date of Patent: Feb. 24, 1998

[54] VENTILATOR/ANAESTHETIC SYSTEM WITH JUXTAPOSED $CO_2$ METER AND EXPIRED GAS FLOW METER

[75] Inventors: Sven-Gunnar Olsson, Arlöv; Göran Rydgren, Bunkeflostrand; Stefan Brauer, Lund; Linge Anders, Kävlinge, all of Sweden

[73] Assignee: Siemens Elema AB, Solna, Sweden

[21] Appl. No.: 606,920

[22] Filed: Feb. 26, 1996

[30] Foreign Application Priority Data

Feb. 27, 1995 [SE] Sweden .................. 950071734

[51] Int. Cl.$^6$ .................. A61M 16/10; A61M 15/00; A62B 7/00; F16K 31/02
[52] U.S. Cl. .................. 128/204.22; 128/203.12; 128/204.21
[58] Field of Search .................. 128/204.21–204.23, 128/205.23, 203.12

[56] References Cited

U.S. PATENT DOCUMENTS

| | | | |
|---|---|---|---|
| 3,927,670 | 12/1975 | Turney et al. | 128/204.22 |
| 4,112,938 | 9/1978 | Jeretin | 128/204.22 |
| 4,188,946 | 2/1980 | Watson et al. | 128/910 |
| 4,509,359 | 4/1985 | Gedeon et al. | 73/23 |
| 4,537,190 | 8/1985 | Caillot et al. | 128/204.22 |
| 4,619,269 | 10/1986 | Cutler et al. | 128/719 |
| 4,648,396 | 3/1987 | Raemer | 128/204.22 |
| 5,072,737 | 12/1991 | Goulding | 128/205.23 |
| 5,094,235 | 3/1992 | Westenskow et al. | 128/204.22 |

FOREIGN PATENT DOCUMENTS 0 392 503  10/1990  European Pat. Off.
0 584 519  3/1994   European Pat. Off.

OTHER PUBLICATIONS

"Operating Manual For Siemens $CO_2$ Analyzer 930." Jul. 1981.

Primary Examiner—Kimberly L. Asher
Attorney, Agent, or Firm—Hill, Steadman & Simpson

[57] ABSTRACT

A number of different parameters related to carbon dioxide output of a patient are routinely determined in ventilator/anaesthetic systems. For this purpose, a ventilator/anaesthetic system for determining carbon dioxide parameters includes a ventilator unit in which a first flow meter is arranged to measure an expired flow of gas, and a carbon dioxide meter is arranged to measure the concentration of carbon dioxide in expired gas. Arranging the carbon dioxide meter in the ventilator/anaesthetic unit minimizes the equipment which must be located in the immediate vicinity of patient, and a faster, more sensitive carbon dioxide meter thus can be used.

7 Claims, 1 Drawing Sheet

VENTILATOR/ANAESTHETIC SYSTEM WITH JUXTAPOSED $CO_2$ METER AND EXPIRED GAS FLOW METER

BACKGROUND OF THE INVENTION

1. Field of the Invention

The present invention relates to a ventilator/anaesthetic system wherein the patient's carbon dioxide output is monitored.

2. Description of the Prior Art

Ventilator/anaesthetic systems are known which in general include a ventilator/anaesthetic unit, an inspiratory tube to carry a breathing gas from the ventilator/anaesthetic unit to a patient, an expiratory tube to carry expired breathing gas from the patient to the ventilator/anaesthetic unit, a patient tube, connected to the inspiratory tube and the expiratory tube and connectable to the patient's airways, a flow meter arranged to measure the flow of expired gas, a carbon dioxide meter to measure the concentration of carbon dioxide in expired breathing gas, and a calculation unit connected to the carbon dioxide meter and the flow meter to determine at least one parameter related to the patient's carbon dioxide output.

Ventilator systems are normally used for supporting or controlling the respiration of patients with respiratory problems or who are incapable of breathing without assistance. The problems can be caused by lung disease or damage to the lungs. Anaesthetic systems are used for inducing anaesthesia in patients about to undergo surgery. With both systems, it is important to obtain some measure on the efficacy of the patient's ventilation. Information as to whether the patient's blood is being oxygenated to a sufficient degree is especially important. One highly useful procedure in this context is to study some parameter related to the patient's carbon dioxide output. One such parameter is end tidal concentration, i.e. the carbon dioxide concentration in the last gas expired by the patient in an expiration phase. The end tidal concentration of carbon dioxide is indicative of arterial blood gas pressure and, accordingly, shows whether or not the patient is being correctly ventilated.

Another parameter related to carbon dioxide output is the minute production of carbon dioxide, normally expressed as an expired volume of carbon dioxide per minute. This parameter is indicative of the patient's general metabolism. Other parameters indicative of the efficacy of patient ventilation are also well-known.

One known carbon dioxide analyzer is described in the Operating Manual for the $CO_2$ Analyzer 930, AG 0291 2.5, July 1981, Siemens-Elema AB. This known carbon dioxide analyzer is connected to a cuvette on the Y-piece of the intubation system connected to the patient. Carbon dioxide is measured using conventional IR spectrophotometry. The analyzer includes a light source, a filter and a detector. The filter allows passage of a light wavelength at which carbon dioxide absorbs the light. Since the analyzer is located in the Y-piece, gas passes the gas cuvette in two directions, i.e. during inspiration, when fresh gas is carried from the ventilator unit to the patient, and during expiration, when gas is carried from the patient in an expiratory tube back to the ventilator unit. At the end of the inspiratory phase, the carbon dioxide analyzer is zeroed to obtain a reference level for 0% carbon dioxide. Zeroing is necessary with this kind of analyzer, since the detector signal would otherwise generate erroneous values for the carbon dioxide concentration.

The placement of the analyzer on the Y-piece makes it necessary to position it near the patient, but since it is heated during operation (to avoid condensation on surfaces through which light must pass) it must not come into contact with the patient's skin. A heat shield is also often used to further protect the patient from the hot analyzer. In addition to heat generation, other problems are associated with this arrangement for a carbon dioxide analyzer. As noted above, the analyzer is zeroed in the final phase of inspiration. Gas supplied to the patient is normally dry, and the zero value for carbon dioxide is therefore for dry air. Before the gas is delivered to the patient's lungs, it can pass a humidifier which humidifies the gas. Regardless of whether a humidifier is used, gas expired by the patient is saturated with water. Gas expired by the patient can also contain secretion etc. Since the carbon dioxide concentration is therefore measured from gas saturated with moisture, for which correction must be made in determinations of the carbon dioxide concentration, the deposition of condensation or secretion on the cuvette's windows, or something else preventing the light beam from passing the cuvette unimpeded, is a risk. Increasing the length of the common tube for inspiration and expiration also increases dead space.

Another problem, which could develop when the carbon dioxide meter is used in anaesthetic systems, is that certain anaesthetic devices operate with closed systems which re-use expired gas. Carbon dioxide is removed from the gas before it is returned to the patient, but inspired gas could still contain small amounts of carbon dioxide, and the carbon dioxide analyzer might therefore be zeroed when the concentration is actually greater than 0%. This would obviously occur also with ventilator systems when ordinary air is supplied to the patient via the ventilator system.

In practice, every manufacturer places the carbon dioxide meter next to the patient, as a matter of principle, so the best possible measurement value is obtained for end tidal concentration. Technical developments have accordingly attempted to minimize and simplify carbon dioxide analyzers, without affecting accuracy, in order to minimize the size of the equipment which needs to be placed near the patient.

In the determination of a plurality of the parameters, such as the volume of expired carbon dioxide, the minute production of carbon dioxide etc., respiratory gas flow is also measured. This is normally performed with a flow meter arranged in the ventilator/anaesthetic unit. Pressure changes in the expiratory tube, however, can cause compression of the volume, and the measured flow will then fail to correspond to the patient's expired flow. Errors also occur in calculations of the parameter.

SUMMARY OF THE INVENTION

An object of the present invention is to provide a ventilator/anaesthetic system in which accurate measurement of parameters related to the patient's carbon dioxide output can be performed while the aforementioned problems are simultaneously resolved.

Such a ventilator/anaesthetic system is achieved in accordance with the invention having a carbon dioxide meter which generates a measurement signal and a reference signal, the carbon dioxide concentration then being determined from the relationship between the measurement signal and the reference signal, the carbon dioxide meter being arranged downstream from the patient tube, near the flow meter, to measure the concentration of carbon dioxide in expired breathing gas. A calculation unit determines the parameter from the values measured for flow and the carbon dioxide concentration in at least two breaths.

Carbon dioxide meters, which generate a measurement signal and a reference signal, are well-known. They can, e.g., be constructed so a filter wheel rotates and alternately interposes different filters in the beam path between the light source and the light detector. One filter then passes a light wavelength at which carbon dioxide absorbs light, and another filter passes a wavelength at which carbon dioxide does not absorb light. Alternately, the number of light detectors can be doubled, and a fixed filter placed in front of the respective detector, each filter passing a specific wavelength. A carbon dioxide meter according to the latter design is disclosed in European Application 0 584 519. Both types of carbon dioxide meters have the advantage of not needing to be zeroed periodically, since they generate a reference signal at a wavelength at which carbon dioxide does not absorb light. This is necessary for obtaining the advantage in the invention of moving the carbon dioxide meter from the Y-piece to the flow meter itself. This means that all the additional equipment related to carbon dioxide measurement is moved away from the patient, thereby greatly facilitating work for staff around the patient. Dead space will also decrease. The measurement instruments can be arranged in different ways. Both the flow meter and the carbon dioxide meter can advantageously be arranged inside the ventilator/ anaesthetic unit.

Another advantage of the new location for the carbon dioxide meter is a reduction in the impact on measurements caused by the patient's moisture-laden expired air, and any secretion in it. Secretion is collected in a special container near the patient, and expired gas can be dehumidified to a greater or lesser degree in a dehumidifier before it reaches the carbon dioxide meter and the flow meter. In addition, prevention of condensation etc. on the windows of the measurement cuvette is facilitated, since the carbon dioxide meter can easily be heated to a much higher temperature at its new location than is acceptable from the safety point of view when located at the Y-piece.

Moving the carbon dioxide meter from the Y-piece, near the patient, to a position close to, or inside, the ventilator/ anaesthetic unit may initially appear a relatively simple measure, since a location near the patient does cause some problems. There are a number of reasons, however, why this has not been possible before. First, the end tidal concentration of carbon dioxide has often been cited as one of the most important carbon dioxide parameters. For correct measurement of this parameter, measurement has been performed as close to the lungs as possible. It must also be remembered that expired gas fills the entire Y-piece and the expiratory tube, like a column of gas, during expiration. The diffusion of gas between breaths obliterates the sharp demarcations at the beginning and end of this gas column. With a system employing continuous flows of gas, i.e. bypass flow, existing gas in the patient tube and expiratory tube is indeed expelled, but it then mixes with gas, which does not occur in the common output of the Y-piece.

This therefore makes it impossible to measure the end tidal concentration of carbon dioxide in a single breath (respiration cycle) when the position of the carbon dioxide meter has been changed. It will be realized that any such change in the position of the carbon dioxide meter is by no means self-evident. A different method for the calculation of the parameters by the calculation unit, and the extraction of same from measurement values, has been needed. This is achieved by virtue of the calculation unit of the invention determining the parameters from values measured for flow and carbon dioxide concentration in at least two respiratory cycles. When the volume of gas in the expiratory tube and Y-piece and the delay until carbon dioxide measurement are known, diffusion in the column of gas can be determined, and the parameters can be corrected. It should be emphasized that continuous measurement throughout two respiratory cycles is not necessary for determining the parameters. Measurement during parts of the cycles is fully sufficient measurement during the measurement periods can be performed in a known manner, e.g. analog (continuous) measurement or digital measurement (with a predefined sampling rate).

A more sensitive carbon dioxide meter can be used when the carbon dioxide meter is placed inside the ventilator/ anaesthetic unit.

Preferably the calculation unit is an integrator and the calculation unit determines a minute volume of carbon dioxide from the integral of the product of the measured carbon dioxide concentration and flow. Compared to known carbon dioxide meters and equipment, a direct product of carbon dioxide concentration and flow can be obtained with a system according to the invention. Since the carbon dioxide meter and flow meter are near each other, the product directly designates the concentration of carbon dioxide in the flow. The integral of the product yields the volume. As noted above, the measurement does not require all the values from two respiratory cycles.

The end tidal concentration, considered in the art as the most interesting parameter, can be determined in at least two ways by the system according to the invention.

The end tidal concentration of carbon dioxide in one breath can be determined as the peak carbon dioxide concentration, measured by the carbon dioxide meter, in the following breath. In principle, the contents of the expiratory tube and patient tube consist of a column of gas. In the final phase of an expiration, there is therefore a column of expired gas in the expiratory tube and the patient tube. During the next inspiration, fresh breathing gas flushes out part of the patient tube and is supplied to the patient. When the patient again exhales, a smaller column of fresh breathing gas, which does not contain any carbon dioxide, pushes the preceding breath's column of gas ahead of it through the ventilator unit and carbon dioxide meter. Measuring the peak value for carbon dioxide concentration in one expiration yields a good value for the end tidal concentration in the preceding breath. One small difference, compared to known measurement systems, may develop because of the diffusion of gas between different gas columns and because of mixing effects between gas columns, if any turbulence occurs. This is not a serious adverse effect, however, since the carbon dioxide curve in expiration rises relatively quickly, as shown in FIG. 1, to a level which is maintained throughout the rest of the expiration, so the true end tidal concentration ($ETCO_2$) does not differ very much, even if there has been some mixture of expired gas and fresh gas. As already noted, diffusion can be determined and calculation of the end tidal concentration can thereby be corrected for that diffusion.

Alternately, the end tidal concentration can be obtained by utilizing the fact that a known volume of expired breathing gas fills the expiratory tube and the patient tube between the carbon dioxide meter and the patient, the calculation unit comprises an integrator for integrating the measurement value from the flow meter and an end tidal concentration of carbon dioxide in one breath is determined as the peak concentration measured by the carbon dioxide meter in the next breath, when a volume corresponding to the known volume has passed the flow meter.

In principle, this method is based on the same reasoning as in the above-described method for obtaining the end tidal concentration. In this instance, however, the known volume is regarded as a unit, and the end tidal concentration is determined at the time the known volume has passed the flow meter.

In practice, the two described methods supply essentially the same value for end tidal concentration. The delay between the end tidal concentration for a specific expiration until measurement of same has occurred, however, can exceed one breath, depending on the tidal volume supplied to the patient and the volumes contained in tubes.

In an embodiment of the ventilator/anaesthetic system in accordance with the invention, the ventilator/anaesthetic system supplies a continuous flow of breathing gas which flows through the inspiratory tube, the patient tube and the expiratory tube, and an additional flow meter is arranged in the ventilator/anaesthetic system, to measure the flow of gas supplied to the inspiratory tube. The additional flow meter supplies a signal to the calculation unit and the calculation unit corrects the parameter's determination from the continuous flow.

Bypass flows occur in different contexts in conjunction with ventilator/anaesthetic systems. For example, a patient, who only requires limited respiratory support in order to breathe, can then breathe, with relative ease, from the passing flow of breathing gas, however, determination of the parameters must be corrected for this continuous flow.

In the case of end tidal concentration, for example, this means that the column of gas which would otherwise have filled the inspiratory tube and part of the patient tube will be expelled more rapidly from the ventilator/anaesthetic system. In addition, this column of gas will mix with fresh gas, thereby affecting measurement of concentration. Since the supplied flow of breathing gas is known, thanks to the additional flow meter, however, the impact of this flow on determination of the parameters can be corrected. The parameter is still determined with measurement values from two respiratory cycles, since the final volume expired by the patient is expelled by the continuous flow following each concluded expiration.

If the volume of the expiratory tube is not known, this volume can be determined by removing the bypass flow for at least one breath and recording when the carbon dioxide value changes. The integral of the value for flow then designates the volume of the tube. Moreover, the curve for the carbon dioxide concentration at the Y-piece can be recreated, with the known tube volume, by correcting for the effect of tube volume.

DESCRIPTION OF THE PREFERRED EMBODIMENTS

As noted above, FIG. 1 shows curves for the concentration of carbon dioxide in air expired by a patient. Curves 2A, 2B and 2C show how the concentration of carbon dioxide rapidly levels off during expiration (exp). At the end of expiration, the concentration rapidly drops towards zero. The end tidal concentration of carbon dioxide, $ETCO_2$, is determined at the end of expiration. During inspiration (insp), the concentration is normally equal to zero.

Figure 2:
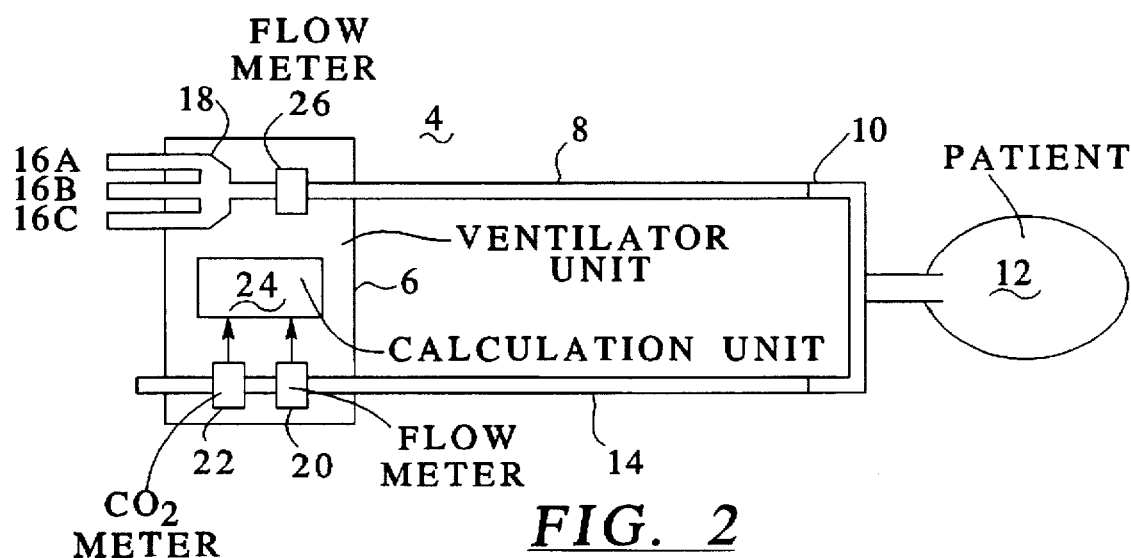
FIG. 2 shows an embodiment of a ventilator system according to the invention.

FIG. 2 shows an embodiment of the invention in the form of a ventilator system 4. The ventilator system 4 includes a ventilator unit 6 from which an inspiratory tube 8 carries a breathing gas, via a patient tube 10, to a patient 12. The patient tube 10 is also referred to as a Y-piece or Y-tube. Expired gas is carried from the patient 12, via the patient tube 10 and an expiratory tube 14, back to the ventilator unit 6. Breathing gas supplied to the patient is admitted via one or more of three gas connections 16A, 16B and 16C and is mixed in a mixing chamber 18 before being carried to the inspiratory tube 8.

Figure 1:
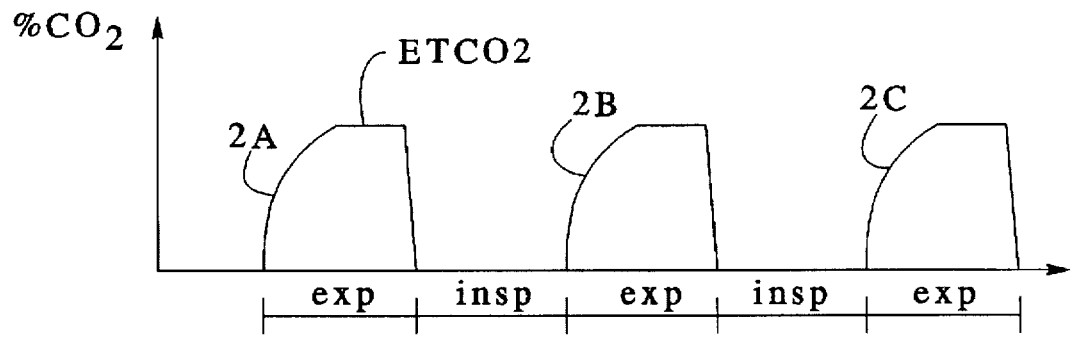
FIG. 1 shows the carbon dioxide concentration during a patient's inspiration and expiration, respectively.

It should be noted that the ventilator unit 6 also has a number of other components than those shown in the FIG. 1. In principle, the ventilator unit 6 can be, e.g., a modified Servo Ventilator 300, Siemens-Elema AB. Check valves can be arranged in the respiratory system to control the direction of gas flow in the inspiratory tube 8, patient tube 10 and expiratory tube 14.

Expired gas passes a first flow meter 20, which is arranged in the ventilator unit 6. The flow of expired gas is measured in this flow meter. A carbon dioxide meter 22 is arranged next to the first flow meter 20. The carbon dioxide meter 22 measures the concentration of carbon dioxide in expired gas. In principle, any carbon dioxide meter will suffice, provided the meter generates a measurement signal and a reference signal, the concentration of carbon dioxide being determined from the ratio between the measurement signal and the reference signal. The carbon dioxide meter 22 is thus an example of carbon dioxide meter means, disposed next to the flow meter 20 downstream from the patient tube 10, for measuring carbon dioxide in expired breathing gas and for generating a measurement signal and a reference signal identifying carbon dioxide in expired breathing gas at respectively different times, including measurement of a peak concentration of carbon dioxide in expired breathing gas. The first flow meter 20 and the carbon dioxide meter 22 are connected to a calculation unit 24, which calculates or determines at least one parameter related to the carbon dioxide output of the patient 12. In the event that a continuous flow of gas is admitted via the inspiratory tube and flows through the patient tube 10 and the expiratory tube 14, a second flow meter 26 is arranged in the ventilator unit calculation unit 24, which can accordingly correct the determination of the parameter, or parameters, for the continuous flow.

Figure 3:
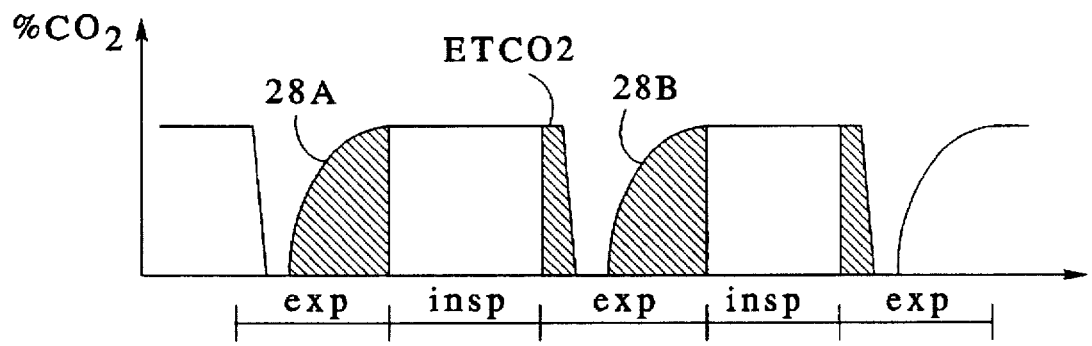
FIG. 3 shows the morphology of a measurement signal from a carbon dioxide meter by the valve system according to the invention.

In contrast to known systems with carbon dioxide meters or carbon dioxide analyzers located in the patient tube 10 near the patient, the calculation unit 24 must be devised to take into account the altered location of the carbon dioxide meter 22. In particular, the fact that there is a given volume of expired gas in the expiratory tube 14 and the patient tube 10 after concluded expiration must be taken into account. This volume of gas does not normally reach the carbon dioxide meter 22 until the next expiration. This is illustrated more clearly in FIG. 3 which shows the measurement signal from the carbon dioxide meter 22 for the expiratory curves shown in FIG. 1. The curve 28A shows that the carbon dioxide meter 22 does not measure gas expired in a breath until some point into the patient's expiration, as shown in the diagram. When the patient terminates an expiration and commences inspiration, the measured concentration of carbon dioxide will remain at a constant level, since gas in the expiratory tube 14 is motionless.

During the next expiration, the volume of gas filling the expiratory tube 14 and part of the patient tube 10 is pushed forward through the carbon dioxide meter 22 and the first flow meter 20. The rest of the gas expired in the preceding breath will then pass the carbon dioxide meter 22, and a value for e.g. the end tidal concentration, $ETCO_2$, can be determined for the preceding breath. This determination can be performed in such a way that the peak value measured for carbon dioxide in each breath serves as the end tidal concentration of carbon dioxide in the preceding breath. Presentation of the end tidal concentration with a delay of one breath is not a major problem for the physician. If some drastic event were to occur in respect to the output of carbon dioxide by the patient 12, it would most likely be manifest even in the part of the curve measured during the current breath. Such an event could be, e.g., failure of the carbon dioxide meter 22 to measure any carbon dioxide content, even though the patient 12 is exhaling.

Other parameters which could de determined are, e.g., effective and ineffective tidal volumes, the minute volume of carbon dioxide in expired gas and the minute production of carbon dioxide by the patient 12. In the same manner as for end tidal concentration, these parameters are determined from information derived from at least two breaths. For example, the minute volume of carbon dioxide in expired gas, which can be determined from the integral of the product of concentration and flow. It then does not matter that the concentration measured during an inspiration is consistently high, since the flow is zero, and flow would have no impact on the determination of the minute volume of carbon dioxide, nor in determination of the minute production of carbon dioxide. Tidal volume is obtained in a corresponding manner by, e.g., integrating the product of concentration and flow for, e.g., the concentration curve 28A.

When a continuous flow of breathing gas flows through the tubes 8, 10 and 14, the calculation unit 24 must correct the calculated parameters for this continuous flow. The most important difference is found in the determination of end tidal concentration, since measurement of concentration alone is then no longer sufficient. The continuous flow will cause the column of gas, or volume of gas, in the expiratory tube 14 at the end of expiration, according to the reasoning above, to be expelled more rapidly from the system. Since the continuous flow is known from the second flow meter 26, the patient flow can be determined as the difference between flows measured in the first flow meter 20 and in the second flow meter 26. Because of the integration, passing volumes are known, and the concentration figure for the entire passing flow, or volume, can be converted into a concentration for the volume of expired gas.

The ventilator system 4 could also employ an anaesthetic system according to some other known design. The salient features of the invention are that measurement of carbon dioxide is made near measurement of flow, and measurement has been transferred to a point downstream from the patient in the direction of expiratory flow.

The calculation unit 24 in the various embodiments is thus an example of calculating means, supplied with the measurement signal, the reference signal and the flow signal, for calculating a concentration of carbon dioxide in expired breathing gas from a ratio of the measurement signal and the reference signal and for calculating a parameter related to production of carbon dioxide by the patient from the concentration and the flow signal over at least two respiratory cycles of the patient. The calculating unit 24 is also an example of calculating means including integrator means for calculating a minute volume of carbon dioxide in expired breathing gas by integrating a product of the production of carbon dioxide and the flow signal, as the aforementioned parameter related to carbon dioxide concentration. The calculation unit 24 is also an example of calculating means including means for determining a peak value for the concentration of carbon dioxide in the expired breathing gas for each respiratory cycle of the patient and for using the peak value in a respiratory cycle as an end title concentration of carbon dioxide in a next successive respiratory cycle. The calculating unit 24 is also an example of calculating means including integrator means for integrating the flow signal and an end title concentration of carbon dioxide in one breath while the carbon dioxide meter 22 measures a peak concentration of carbon dioxide in expired breathing gas in a next breath, after a volume of expired breathing gas equal to the known volume has passed the flow meter 20. Lastly, the calculation unit 24 is an example of calculating means including means for correcting, dependent on the further flow signal received from the flow meter 26, the aforementioned parameter related to carbon dioxide concentration in expired breathing gas.

Although modifications and changes may be suggested by those skilled in the art, it is the intention of the inventors to embody within the patent warranted hereon all changes and modifications as reasonably and properly come within the scope of their contribution to the art.

We claim as our invention:

1. A ventilator/anaesthetic system comprising:
   a ventilator/anaesthetic unit;
   an inspiratory tube connected to said ventilator/anaesthetic unit and adapted for communication with a patient for carrying a breathing gas from said ventilator/anaesthetic unit to a patient;
   an expiratory tube connected to said ventilator/anaesthetic system and adapted for communication with a patient for carrying expired breathing gas from a patient to said ventilator/anaesthetic unit;
   a patient tube connected to said inspiratory tube and to said expiratory tube and adapted for connection to airways of a patient;
   a flow meter disposed downstream of said patient tube for measuring a flow of expired breathing gas and for generating a flow signal corresponding to said flow of expired breathing gas;
   carbon dioxide meter means, juxtaposed to said flow meter downstream from said patient tube, for measuring carbon dioxide in expired breathing gas and for generating a measurement signal and a reference signal identifying carbon dioxide in expired breathing gas at respectively different times; and
   calculating means, supplied with said measurement signal, said reference signal and said flow signal, for calculating a concentration of carbon dioxide in expired breathing gas from a ratio of said measurement signal and said reference signal and for calculating a parameter related to production of carbon dioxide by a patient from said concentration and said flow signal over at least two respiratory cycles of a patient.

2. A ventilator/anaesthetic system as claimed in claim 1 wherein said carbon dioxide meter means are disposed inside said ventilator/anaesthetic unit.

3. A ventilator/anaesthetic system as claimed in claim 1 wherein said expiratory tube has a first end connected to said patient tube and an opposite, second end, and wherein said carbon dioxide meter means is disposed downstream of said second end of said expiratory tube.

4. A ventilator/anaesthetic system as claimed in claim 1 wherein said calculating means comprises integrator means for calculating a minute volume of carbon dioxide in expired breathing gas by integrating a product of said production of carbon dioxide and said flow signal, as said parameter related to carbon dioxide concentration.

5. A ventilator/anaesthetic system as claimed in claim 1 wherein said calculating means comprises means for determining a peak value for said concentration of carbon dioxide in expired breathing gas for each respiratory cycle of a patient and for using the peak value in a respiratory cycle as an end tidal concentration of carbon dioxide in a next successive respiratory cycle.

6. A ventilator/anaesthetic system as claimed in claim 1 wherein said expiratory tube and said patient tube have a combined length extending between said carbon dioxide meter means and a patient, and wherein said combined length contains a known volume of expired breathing gas, and wherein said calculating means comprises integrator means for integrating said flow signal and an end tidal concentration of carbon dioxide in one breath while said carbon dioxide meter means measures a peak concentration of carbon dioxide in expired breathing gas in a next breath, after a volume of expired breathing gas equal to said known volume has passed said flow meter.

7. A ventilator/anaesthetic system as claimed in claim 1 wherein said ventilator/anaesthetic unit comprises means for supplying a continuous flow of breathing gas to said inspiratory tube, and said ventilator/anaesthetic system further comprising a further flow meter disposed for measuring a flow of breathing gas supplied to said inspiratory tube, said further flow meter generating a further flow signal corresponding to said flow of breathing gas supplied to said inspiratory tube, and wherein said calculating means comprises means for correcting, dependent on said further flow signal, said parameter related to carbon dioxide concentration in expired breathing gas.

* * * * *